(12) United States Patent
Kroll et al.

(10) Patent No.: US 7,570,995 B1
(45) Date of Patent: Aug. 4, 2009

(54) METHOD FOR REFORMING A CAPACITOR IN AN IMPLANTABLE MEDICAL DEVICE

(75) Inventors: Mark Kroll, Simi Valley, CA (US); Thomas F. Strange, Easley, SC (US); Gary D. Thompson, Simpsonville, SC (US)

(73) Assignee: Pacesetter, Inc., Sunnyvale, CA (US)

( * ) Notice: Subject to any disclaimer, the term of this patent is extended or adjusted under 35 U.S.C. 154(b) by 532 days.

(21) Appl. No.: 10/966,722

(22) Filed: Oct. 14, 2004

(51) Int. Cl.
*A61N 1/00* (2006.01)
(52) U.S. Cl. .......................................... 607/5
(58) Field of Classification Search ................ 607/1–5, 607/36; 323/299
See application file for complete search history.

(56) References Cited

U.S. PATENT DOCUMENTS

| | | | | |
|---|---|---|---|---|
| 5,222,480 A | * | 6/1993 | Couche et al. ............. | 607/5 |
| 5,741,307 A | * | 4/1998 | Kroll ........................ | 607/5 |
| 5,792,188 A | | 8/1998 | Starkweather et al. ..... | 607/5 |
| 6,096,062 A | | 8/2000 | Silvian ...................... | 607/5 |
| 6,283,985 B1 | | 9/2001 | Harguth et al. ............ | 607/1 |
| 7,030,597 B2 | * | 4/2006 | Bruno et al. .............. | 323/299 |
| 2002/0095186 A1 | | 7/2002 | Harguth et al. ............ | 607/5 |

\* cited by examiner

*Primary Examiner*—George Manuel
(74) *Attorney, Agent, or Firm*—Theresa A. Takeuchi; Steven M. Mitchell

(57) ABSTRACT

The present invention provides a method for reforming a capacitor of an implantable medical device, such as an implantable cardioverter defibrillator, wherein the capacitor has a nominal voltage. The method of reforming the capacitor comprises charging the capacitor to a first voltage that is above the nominal voltage of the capacitor, partially discharging the capacitor through system leakage, charging the capacitor to a second voltage that is above the nominal voltage, and discharging the capacitor through system leakage until the charge on the capacitor dissipates. The present invention also provides an implantable medical device having a capacitor reforming circuit for reforming the capacitor. Capacitors reformed according to the present invention have reduced charge time deformation compared to capacitors conventionally reformed at the nominal voltage.

29 Claims, 13 Drawing Sheets

METHOD FOR REFORMING A CAPACITOR IN AN IMPLANTABLE MEDICAL DEVICE

BACKGROUND OF THE INVENTION

1. Field of the Invention

The present invention relates to a method of reforming a capacitor in an implantable medical device, such as an implantable cardioverter defibrillator (ICD). The present invention also relates to a capacitor reformed by the method of the invention and an implantable medical device incorporating a capacitor reformed by the method of the invention. The present invention further relates to an implantable medical device having reforming circuitry for reforming the capacitor in the implantable medical device.

2. Background Art

Compact, high voltage capacitors are utilized as energy storage reservoirs in many applications, including implantable medical devices. Implantable medical devices include implantable cardiac devices such as, for example, pacemakers, cardioverters and defibrillators. The term "implantable cardioverter defibrillator" or simply "ICD" is used herein to refer to any implantable cardiac device or implantable cardioverter defibrillator ("ICD").

ICDs are typically implanted in patients suffering from potentially lethal cardiac arrhythmias. Arrhythmia, meaning "without rhythm," denotes any variance from normal cardiac rhythm. Heartbeat irregularities are fairly common and many are harmless. A severe heartbeat irregularity known as ventricular tachycardia refers to a runaway heartbeat.

Fibrillation is an irregular rhythm of the heart caused by continuous, rapid, electrical impulses being emitted/discharged at multiple locations known as foci in the heart's atria and ventricles. Because a fibrillating heart is unable to properly pump blood through a patient's body, the longer a patient is in fibrillation, the greater the potential damage that can occur to the patient's heart. Thus, after the start of fibrillation, it is preferable to apply defibrillating therapy to the patient as soon as possible. An ICD is designed to apply such therapy automatically and quickly to minimize damage to the heart.

An ICD monitors cardiac activity and decides whether electrical therapy is required. For example, if a tachycardia is detected, pacing or cardioversion therapy may be used to terminate the arrhythmia. If fibrillation is detected, defibrillation is the only effective therapy.

Typical ICDs include a set of electrical leads, which extend from a sealed housing into the walls of a heart after implantation. Within the housing are a battery for supplying power, a capacitor for delivering bursts of electric current through the leads to the heart, and monitoring circuitry for monitoring the heart and determining when, where, and what electrical therapy to apply. The monitoring circuitry generally includes a microprocessor and a memory that stores instructions not only dictating how the microprocessor controls delivery of therapy, but also controlling certain device maintenance functions, such as maintenance of the capacitors in the device.

Electrolytic capacitors are used in ICDs because they have the most nearly ideal properties in terms of size, reliability and ability to withstand relatively high voltage. Typically, these capacitors can be aluminum electrolytic capacitors having aluminum foil plates. Current ICDs usually contain two aluminum electrolytic capacitors for shock delivery.

It is important that the anode foil used in these capacitors maintains a high capacitance with the lowest possible leakage current. The term "leakage current" refers to the current passing from the cathode plate through an electrolyte and across the anodic oxide dielectric into the aluminum foil. Under conventional anode foil preparation techniques, a barrier oxide layer is formed onto one or both surfaces of a metal foil. The oxide film must be sufficiently thick to support the intended use voltage for shock delivery (referred to hereinafter as the "nominal voltage"). This oxide film acts as a dielectric layer for the capacitor, and constitutes a barrier to the flow of current between the electrolyte and the metal foil, thereby providing a high resistance to leakage current passing between the anode and cathode foils. However, a small amount of current, the leakage current, still passes through the barrier oxide layer due to intrinsic defects in the crystalline oxide, and electron injection from the electrolyte rather than oxide injection into the dielectric. A high leakage current can result in the poor performance and reliability of an electrolytic capacitor. In particular, a high leakage current results in a greater amount of charge lost internally to the capacitor once it has been charged.

Both cardioversion and defibrillation require that a high voltage shock be delivered to the heart. Since ICDs are typically powered by a battery implanted in a patient's body, it is usually impractical to maintain full voltage continuously ready for use. To conserve battery energy, ICDs normally charge energy storage capacitors after detection of an arrhythmia and prior to delivering a shock to the heart.

To shorten the time between arrhythmia onset and therapy, pulse discharge capacitors such as those in ICDs are required to charge quickly after protracted storage in the discharged state. However, leaving the capacitors in an uncharged state leads to degradation of the aluminum oxide on the capacitors over time. Instability of the aluminum oxide in the liquid electrolyte results in degradation over time of the charging efficiency of the capacitor. For this reason, ICDs containing aluminum electrolytic capacitors typically also include capacitor maintenance software to periodically reform the aluminum oxide on the aluminum electrolytic capacitors. The periodic reformation process serves to replenish the oxide and reduce the leakage current of the aluminum electrolytic capacitors. This, in turn, reduces charge time of the capacitors the first time that they are needed for therapeutic use after an extended period of non-use.

Conventionally, the reformation process consists of charging the aluminum electrolytic capacitors to the device's nominal voltage and then allowing the charge to dissipate.

A Capacitor Maintenance Interval is generally established with a range of 1-6 months. When the Capacitor Maintenance Interval times out, the device performs Capacitor Maintenance. Typically, Capacitor Maintenance consists of the ICD's software requesting charging of the capacitors to the device's nominal voltage. After the Capacitor Maintenance charge to the device's nominal voltage is completed, the Capacitor Maintenance Interval is restarted. The charge on the capacitors is allowed to dissipate by leaking through some parasitic discharge path. Alternatively, the ICDs may be programmed to dump the capacitor charge into an internal load.

Various other systems for capacitor maintenance exist, including automatic capacitor maintenance systems such as those described in U.S. Pat. No. 5,861,006 to Kroll, and U.S. Pat. No. 5,899,923 to Kroll et al., which are incorporated herein by reference in their entirety.

BRIEF SUMMARY OF THE INVENTION

The present invention provides an improved process for reforming the capacitors of an implantable medical device, such as an implantable cardioverter defibrillator. According to one embodiment of the present invention, a method for reforming a capacitor of an implantable medical device wherein the capacitor has a nominal voltage for shock delivery comprises charging the capacitor to a voltage above the nominal voltage. In one embodiment of the present invention, the method for reforming a capacitor of an implantable medical device wherein the capacitor has a nominal voltage comprises the steps of: (a) charging the capacitor to a first voltage above the nominal voltage of the capacitor; (b) partially discharging the capacitor; (c) charging the capacitor to a second voltage above the nominal voltage of the capacitor; and (d) discharging the capacitor. Discharging can be performed through system leakage or a non-therapeutic load (dump onto an internal load), or other processes known to those skilled in the art.

The capacitors reformed according to the method of the present invention have decreased charge time deformation compared to conventional capacitors reformed at the nominal voltage.

The present invention also provides a capacitor reformed according to the method of the invention and an implantable medical device incorporating a capacitor reformed according to the method of the invention. The present invention further provides an implantable medical device comprising a capacitor having a nominal voltage and a capacitor reforming circuit for reforming the capacitor at a voltage above the nominal voltage.

Further features and advantages of the present invention, as well as the structure and operation of various embodiments of the present invention, are described in detail below with reference to the accompanying drawings.

BRIEF DESCRIPTION OF THE DRAWINGS/FIGURES

The accompanying drawings, which are incorporated herein and form part of the specification, illustrate the present invention and, together with the description, further serve to explain the principles of the present invention and to enable a person skilled in the pertinent art to make and use the invention.

DETAILED DESCRIPTION OF THE INVENTION

Figure 1:
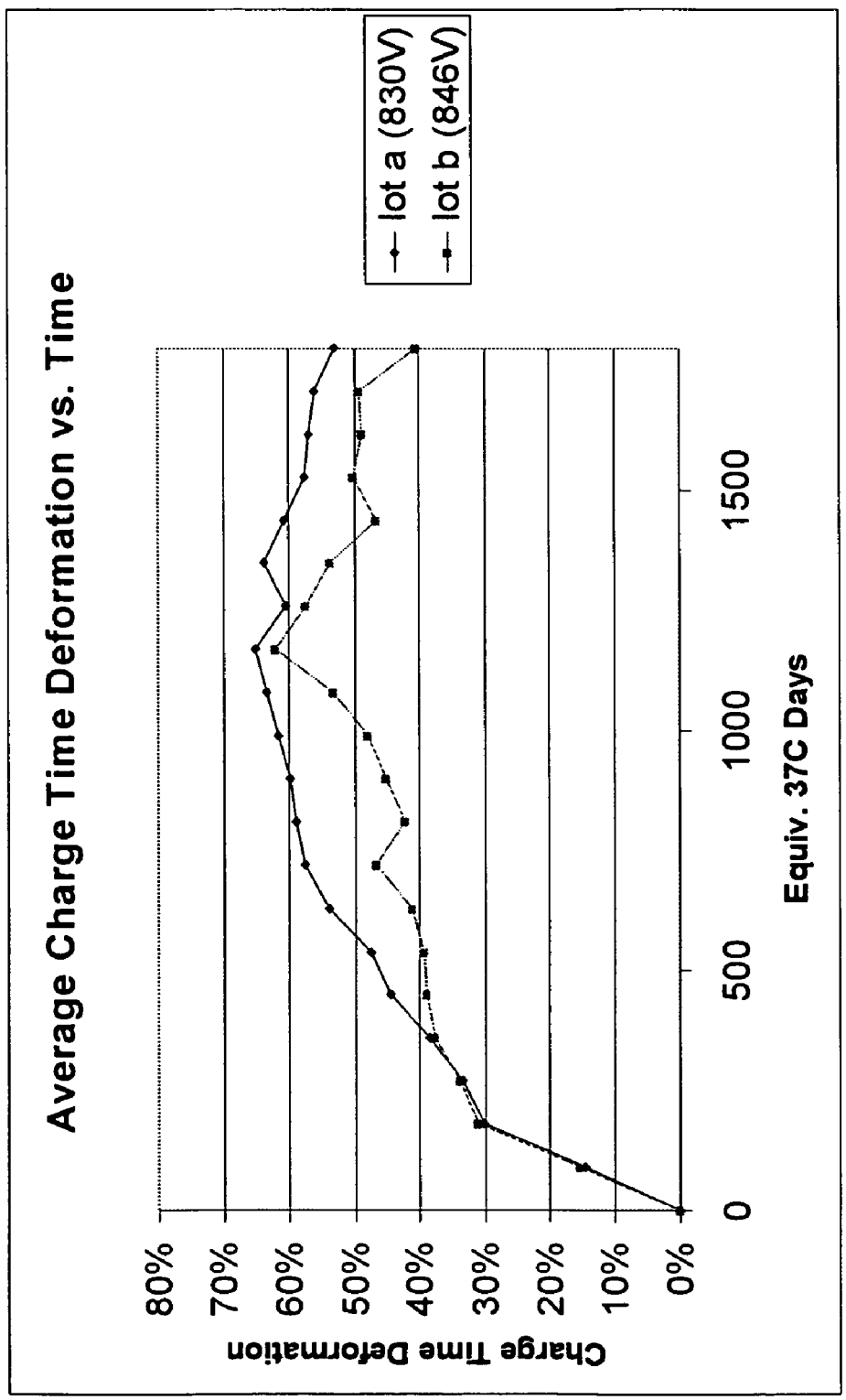
FIG. 1 shows the effects of higher reform voltages according to the present invention on charge time deformation for capacitors reformed at 3-month reform intervals.

The present invention relates to a process for reforming a capacitor of an implantable medical device. The present invention also provides a capacitor reformed by the method described herein, and an implantable medical device comprising a capacitor reformed by the method described herein. The present invention further relates to an implantable medical device having a reforming circuit for reforming the capacitors.

Preferred embodiments of the present invention are now described. While specific configurations and arrangements are discussed, it should be understood that this is done for illustrative purposes only. A person skilled in the relevant art will recognize that other configurations and arrangements can be used without departing from the spirit and scope of the invention. It will also be apparent to a person skilled in the relevant art that this invention can be employed in a variety of other devices and applications.

Conventional aluminum electrolytic capacitors are normally reformed by periodically charging the capacitors to a nominal voltage. Various methods have been proposed for reforming the capacitors in an effort to decrease the degradation of the capacitor oxide while conserving as much battery energy as possible.

Deformation is the degradation of the aluminum oxide due to mild attack by the fill electrolyte while the capacitor is uncharged. This effect increases with time and temperature but is reversed by charging the capacitor. The degradation results in a temporary increase in charge time.

According to the present invention, a method for reforming a capacitor of an implantable medical device wherein the capacitor has a nominal voltage comprises charging the capacitor to a voltage that is above the nominal voltage.

In one embodiment of the present invention, the reforming of the capacitor further comprises the step of discharging the capacitor through system leakage after the charging of the capacitor. Alternatively, the step of discharging can be performed through a non-therapeutic load or other processes known to those skilled in the art.

When the capacitors are charged to a voltage above the nominal voltage and allowed to dissipate by leaking through a parasitic discharge path, the capacitor voltage will fall more quickly than if the capacitor charge is dumped into an internal (i.e., dummy) load. The system leakage or discharge path includes leakage internal to the capacitor as well as leakage through a measurement circuit that has an impedance of approximately 20 MΩ. This system leakage is also referred to as the "droop" or "bleed down" of the charge.

In another embodiment of the present invention, the reforming of the capacitor comprises the steps of (a) charging the capacitor to a first voltage that is above the nominal voltage of the capacitor; (b) partially discharging the capacitor; and (c) charging the capacitor to a second voltage that is above the nominal voltage of the capacitor after the partial discharging step. Preferably, the discharging step is performed through system leakage and is carried out for about 2 seconds to about 300 seconds, and preferably for about 4 seconds to about 30 seconds. More preferably, the discharging step is performed through system leakage and is carried out for about 10 seconds. Alternatively, the partial discharging is performed through a non-therapeutic load.

In a further embodiment of the present invention, the reforming of the capacitor further comprises the step of fully discharging the capacitor after charging the capacitor to the second voltage. According to one embodiment of the present invention, the discharging step after the second charge, is performed through system leakage and is carried out until the charge on the capacitor dissipates. Alternatively, this discharging step after the second charge is performed through a non-therapeutic load. In one embodiment of the present invention, the discharging step after the second charge is performed through system leakage and is carried out for about 4 seconds to about 300 seconds, followed by discharging the capacitor through a non-therapeutic load.

In one embodiment, the reforming of the capacitor according to the method of the present invention is performed periodically, once after the passing of a capacitor maintenance interval. The capacitor maintenance interval is preferably between 1 to 6 months. For example, the capacitor maintenance interval may be 3-months, 4-months, or 6-months.

According to another embodiment of the present invention, the reforming of the capacitor comprises charging the capacitor to a voltage that is about 1% to about 6% higher than the nominal voltage of the capacitor. For example, two capacitors in series having a total nominal voltage of about 830 volts can be reformed by charging the capacitors to a voltage of about 840 volts to about 880 volts according to the method of the present invention. In one preferred embodiment of the present invention, the capacitors are reformed by charging the capacitors to about 860 volts. In another preferred embodiment of the present invention, the capacitors are reformed by charging the capacitors to about 880 volts.

In a preferred embodiment of the present invention, the method for reforming a capacitor of an implantable medical device wherein the implantable medical device comprises two capacitors in series having a total nominal voltage of about 830 volts comprises the steps of: (a) charging the capacitors to a first voltage of about 860 or about 880 Volts; (b) partially discharging the capacitors for about 10 seconds through system leakage; (c) charging the capacitors to a second voltage of about 860 or about 880 Volts; and (d) discharging the capacitors through system leakage until the charge on the capacitors dissipates.

Capacitors that are reformed by the steps of charging the capacitors to a voltage above nominal voltage, allowing the capacitors to droop, and charging the capacitors again to a second voltage above nominal voltage, have decreased charge times and charge time deformation when compared to capacitors that are reformed with a single nominal charge. In an alternative embodiment, capacitors that are reformed with a second charge to a nominal voltage also have decreased charge times and charge time deformation when compared to capacitors that are reformed with a single charge to nominal voltage.

For example, capacitors that were reformed every 3-months of accelerated life according to the present invention had a decrease in the charge time deformation effect from 59.76% to 45.09% at 2.5 years of accelerated life and from 52.88% to 40.44% at 5 years of accelerated life when the reform voltage was increased from a nominal voltage of 830V to a surge voltage of 846V.

In another example, capacitors that were reformed every 3-months of accelerated life according to the present invention and charged to a surge voltage of 846V had a decrease in the charge time deformation effect from 45.09% to 40.38% at 2.5 years of accelerated life and from 40.44% to 32.05% at 5 years of accelerated life when the capacitors were allowed to droop for 30 seconds before dumping the charge.

In a further example, capacitors that were reformed every 3-months of accelerated life according to the present invention and charged to a surge voltage of 846V had a decrease in the charge time deformation effect from 40.38% to 32.92% at 2.5 years of accelerated life and from 32.05% to 27.91% at 5 years of accelerated life when an additional charge step was added to each 3-months of accelerated life.

In another example, capacitors that were reformed every 6-months of accelerated life according to the present invention and which did not contain additional droop time before the charge on the capacitors was dumped had a decrease in the charge time deformation effect from 57.94% to 54.09% at 2.5 years of accelerated life and from 71.80% to 56.60% at 5 years of accelerated life when the reform voltage was increased from a nominal voltage of 830V to a surge voltage of 846V.

The present invention also provides an implantable medical device comprising a capacitor having a nominal voltage and capacitor reforming circuit for reforming the capacitor at a reforming voltage that is above the nominal voltage. The reforming circuit carries out the reforming steps according to various embodiments of the method of the present invention. Examples of reforming circuits are shown in U.S. Pat. No. 5,861,006 to Kroll, and U.S. Pat. No. 5,899,923 to Kroll et al.

EXAMPLES

Example 1

Aluminum Electrolytic capacitors were reformed using various charging profiles and the charge time deformation of the capacitors was determined after each time interval that is the accelerated equivalent of the time interval between maintenance charges that the ICD delivers to the capacitors.

In order to simulate the accelerated equivalent of the time interval between maintenance charges that the ICD delivers to the capacitor (hereinafter referred to as a "down"), the capacitors were placed in a 90° C. oven for 16 hours. Each down in this example is the accelerated equivalent of about 90 days implanted at 37° C. The charge time deformation of the capacitors were measured for 20 downs, which is approximately the accelerated equivalent of about 5 years in a patients body.

Twenty-one (21) aluminum electrolytic capacitor pairs were tested. Prior to determining charge times of the capacitors reformed according to various tested charging profiles, the capacitors were baseline tested using the MCT (Multiple Capacitor Tester) Forming and Discharge test, which measures LC1 (leakage current), CE1 (charge efficiency), DP1 (droop), SE1 (stored energy), Elec3 (maximum surge voltage) and ST1 (pulse test, 7 pulses).

The leakage current test involves charging capacitors in parallel at 10 to 60 mA constant current per capacitor to a specified voltage, preferably at 50 mA per capacitor charging current. The capacitors are held at that voltage for a specified amount of time and the leakage currents at specified time intervals after charge are measured. Then each capacitor is discharged singularly into a specified load resistor. Maximum surge voltage is determined from a leakage current test wherein the specified charge voltage is equivalent to maximum surge voltage.

The stored energy and charge efficiency (or delivered energy) tests involve performing a charge/discharge test at specific parameters. The charge/discharge test involves charging the capacitor assembly to a specified voltage with a constant power charge, $P_{ch}$. Then, the capacitor assembly is allowed to droop for a specified amount of time and then discharged into a specified load resistor. Charge energy is derived by integrating the power curve obtained during the charge cycle. Discharge energy is measured by integrating the area under the capacitor discharge power curve from the start of discharge until the specified stopping point. Capacitor charging efficiency is calculated by dividing the discharge energy measured by the charge energy measured. The droop test involves charging the capacitor to a specified voltage at constant power, $P_{ch}$. The charge circuit is then disconnected and the capacitor allowed to droop for a specified amount of time with no load. The voltage at droop intervals is measured. Then, capacitors are discharged into a specified load resistor. The voltage measurement circuit provides a 10 MΩ load to the capacitor under test. The droop voltage is reported as the change in voltage from the start voltage to the voltage at the droop period.

In the pulse test, all capacitors may be charged in parallel at a minimum 10 mA to 60 mA maximum constant current per capacitor source until the capacitor reaches the specified voltage. Then each capacitor is individually discharged into a 15Ω load. This cycle is repeated a specified amount of times. No measurements need to be taken during this test.

Test parameters for the pulse test include, for example, 7 cycles, a charge voltage equal to the nominal operating voltage of the capacitor, and a resistance load of 15Ω for a capacitor assembly or a single capacitor.

The capacitors were charged at the voltage corresponding to the Beginning of Life (BOL) condition of the battery (3.20V) and the Elective Replacement Indicator (ERI) condition of the battery (2.45V). The BOL condition occurs when the battery is early in its lifecycle. The power supply that is simulating the BOL condition of the battery is set to 3.20V. The ERI condition occurs when the battery is at the end of its lifecycle. The power supply that is simulating the ERI battery condition is set to 2.45V.

The BOL baselines and ERI baselines were measured using a breadboard charger. A breadboard charger is a device constructed in order to simulate the ICD Hybrid functionality (i.e. constant power charging circuit for the capacitor, battery connections to the breadboard charger, etc.).

Using the breadboard, all capacitors were charged three times at BOL and ERI battery conditions and the breadboard charge times were recorded. The charge times at ERI battery condition was the baseline used to calculate the percent deformation for each accelerated life down. Table 1 shows an average of the charge times obtained for each test lot when capacitors were charged at BOL battery condition and an average of the charge times obtained for each test lot when capacitors were charged at ERI battery condition

TABLE 1

BOL and ERI baselines

| Lot No. | BOL baseline charge time (s) | ERI baseline charge time (s) |
|---|---|---|
| A | 6.80 | 10.67 |
| B | 6.65 | 10.63 |
| C | 6.67 | 10.40 |
| D | 6.67 | 10.63 |
| E | 6.56 | 10.53 |
| F | 6.71 | 10.57 |
| G | 6.56 | 10.60 |
| Ta | 7.32 | 11.60 |

For each down, the capacitors were placed in a 90° C. oven for 16 hours (the accelerated equivalent of 37° C. for 90 days). After the time expired, the capacitor pairs were removed from the oven and placed in a body box until the capacitors were at 37° C. The capacitors were then reformed in accordance with the designated reformation charging profiles. The twenty-one (21) aluminum electrolytic capacitor pairs were randomly divided into seven (7) different test lots, each with a different charging profile, as follows:

Lot A—Control lot that, for each 3-month 37° C. equivalent down, was breadboard charged at ERM battery condition to a nominal voltage of 830V and then dumped.

Lot B—Test lot that, for each 3-month 37° C. equivalent down, was breadboard charged at ERI battery condition to a surge voltage of 846V and then dumped.

Lot C—Test lot that, for each 3-month 37° C. equivalent down, was breadboard charged at ERI battery condition to a surge voltage of 846V, allowed to bleed down for 30 seconds and then dumped.

Lot D—Test lot that, for each 3-month 37° C. equivalent down, was breadboard charged at ERI battery condition to a surge voltage of 846V, allowed to bleed down for 30 seconds, charged to a surge voltage of 846V again, allowed to bleed down for 30 seconds and then dumped.

Lot E—Test lot that, for each 3-month 37° C. equivalent down, was breadboard charged at ERI battery condition to 875V, allowed to bleed down for 30 seconds and then dumped.

Lot F—Test lot that, for each 6-month 37° C. equivalent down, was breadboard charged at ERI battery condition to a nominal voltage of 830V and then dumped.

Lot G—Test lot that, for each 6-month 37° C. equivalent down, was breadboard charged at ERI battery condition to a surge voltage of 846V and then dumped.

Lot Ta—A Tantalum capacitor ("lot ta") was included in this test as a comparison point.

The charge time that was required to charge the capacitors to a nominal voltage of 830V was then measured and the charge time deformation was determined.

The charge time and charge time deformation were measured at each down and an average of the measurements obtained for each test lot was calculated. Table 2 shows the average charge times for each test lot. Table 3 shows the average charge time deformation percentages for each lot.

TABLE 2

Charge Times (Seconds)

| 37° C. days | lot A (s) | lot B (s) | lot C (s) | lot D (s) | lot E (s) | lot F (s) | lot G (s) | lot Ta (s) |
|---|---|---|---|---|---|---|---|---|
| 90 | 12.2 | 12.27 | 12.13 | 12.13 | 12.53 | | | 14.2 |
| 180 | 13.87 | 13.93 | 13.3 | 13.13 | 14 | 13.47 | 13.63 | 14.2 |
| 270 | 14.23 | 14.23 | 13.73 | 13.3 | 14.13 | | | 14.5 |
| 360 | 14.77 | 14.63 | 13.93 | 13.4 | 13.77 | 14.17 | 14.27 | 14.9 |
| 450 | 15.4 | 14.77 | 13.93 | 13.9 | 13.93 | | | 15.3 |
| 540 | 15.73 | 14.83 | 14.17 | 13.47 | 13.87 | 14.83 | 14.6 | 15.4 |
| 630 | 16.4 | 15 | 14.3 | 13.67 | 14.07 | | | 15.8 |
| 720 | 16.8 | 15.6 | 14.7 | 13.73 | 14 | 15.73 | 15.33 | 15.7 |
| 810 | 16.93 | 15.13 | 14.77 | 13.67 | 14.33 | | | 15.8 |
| 900 | 17.03 | 15.43 | 14.6 | 14.13 | 14.27 | 16.7 | 16.33 | 16.1 |
| 990 | 17.23 | 15.73 | 14.43 | 14.07 | 14.9 | | | 16.3 |
| 1080 | 17.4 | 16.3 | 15.33 | 14.2 | 14.97 | 16.47 | 15.9 | 16.5 |
| 1170 | 17.6 | 17.23 | 15.4 | 14.6 | 14.8 | | | 16.8 |
| 1260 | 17.1 | 16.73 | 15.4 | 15.1 | 14.8 | 18.4 | 18.67 | 16.8 |
| 1350 | 17.47 | 16.33 | 15.47 | 14.93 | 15.13 | | | 16.7 |
| 1440 | 17.13 | 15.6 | 14.3 | 14.17 | 14.47 | 18.17 | 16.87 | 16.7 |
| 1530 | 16.8 | 15.97 | 14.5 | 14.2 | 14.27 | | | 16.6 |
| 1620 | 16.73 | 15.83 | 14.17 | 14 | 14.77 | 18.13 | 17.13 | 16.5 |
| 1710 | 16.63 | 15.87 | 14.1 | 13.97 | 14.33 | | | 16.6 |
| 1800 | 16.3 | 14.93 | 13.73 | 13.6 | 14.13 | 18.17 | 16.6 | 16.8 |

TABLE 3

Charge Time Deformation

| 37° C. days | lot A | lot B | lot C | lot D | lot E | lot F | lot G | lot Ta |
|---|---|---|---|---|---|---|---|---|
| 90 | 14.40% | 15.40% | 16.67% | 14.10% | 18.99% | | | 22.41% |
| 180 | 30.03% | 30.97% | 27.88% | 23.50% | 32.92% | 27.45% | 28.62% | 22.41% |
| 270 | 33.47% | 33.86% | 32.05% | 25.07% | 34.17% | | | 25.00% |
| 360 | 38.49% | 37.56% | 33.97% | 26.02% | 30.73% | 34.04% | 34.59% | 28.45% |
| 450 | 44.41% | 38.82% | 33.97% | 30.72% | 32.31% | | | 31.90% |
| 540 | 47.53% | 39.44% | 36.22% | 26.64% | 31.66% | 40.35% | 37.74% | 32.76% |
| 630 | 53.82% | 41.01% | 37.50% | 28.53% | 33.57% | | | 36.21% |
| 720 | 57.55% | 46.60% | 41.35% | 29.15% | 32.93% | 48.83% | 44.65% | 35.34% |
| 810 | 58.81% | 42.24% | 41.99% | 28.53% | 36.08% | | | 36.21% |
| 900 | 59.76% | 45.09% | 40.38% | 32.92% | 35.45% | 57.94% | 54.09% | 38.79% |
| 990 | 61.64% | 47.91% | 38.78% | 32.28% | 41.45% | | | 40.52% |
| 1080 | 63.20% | 53.26% | 47.44% | 33.54% | 42.08% | 55.73% | 50.00% | 42.24% |
| 1170 | 65.09% | 62.01% | 48.08% | 37.30% | 40.51% | | | 44.83% |
| 1260 | 60.38% | 57.28% | 48.08% | 41.80% | 40.54% | 74.00% | 76.10% | 44.83% |
| 1350 | 63.83% | 53.62% | 48.72% | 40.44% | 43.66% | | | 43.97% |
| 1440 | 60.70% | 46.62% | 37.50% | 33.24% | 37.36% | 71.78% | 59.12% | 43.97% |
| 1530 | 57.57% | 50.10% | 39.42% | 33.54% | 35.43% | | | 43.10% |
| 1620 | 56.95% | 48.84% | 36.22% | 31.67% | 40.19% | 71.47% | 61.64% | 42.24% |
| 1710 | 56.00% | 49.20% | 35.58% | 31.35% | 36.07% | | | 43.10% |
| 1800 | 52.88% | 40.44% | 32.05% | 27.91% | 34.16% | 71.80% | 56.60% | 44.83% |

Breadboard Charging Current—The Breadboard normally draws the full 2.90 A from the power supply when charging capacitors at the battery BOL condition. When the condition changes to ERI the Breadboard draws around 2.6 A. The decrease in current occurs because the chips on the Breadboard require a minimum voltage and once the voltage drop across the 0.200Ω Equivalent Series Resistance (ESR) is subtracted from the ERI battery voltage (2.45V), that threshold is breached.

The ICD battery has an ESR of 0.200Ω so a 0.200Ω resister is placed in series between the power supply and the Breadboard input terminals. The internal ESR resistor on the Breadboard (R100) is a 0.300Ω resistor that must be shorted prior to operation.

The Breadboard limits the current (which in turn limits the voltage drop across the ESR) until the chips have their proper operating voltage again. Due to limitations with the Breadboard that was used in this experiment, only 2.65 A and 2.3 A respectively were achieved on the BOL and ERI battery conditions. This decrease in current to the charging circuit represents a decrease in charging current to the capacitor, which also represents an increase in charge time/deformation measurements. For this reason, the absolute value of the deformation percentages are higher than expected for this test but since all capacitors were tested in equivalent methods, conclusions can be drawn about which reform strategy produced the lower relative deformation percentages.

FIGS. 1-6 are graphs of the results obtained in this experiment. As can be seen from FIG. 1, the graphical plots of average charge time deformation vs. equivalent 37° C. days for Test lots A and B show a significant improvement when reforming the capacitors to a Surge voltage of 846V vs. a Nominal voltage of 830V.

Figure 2:
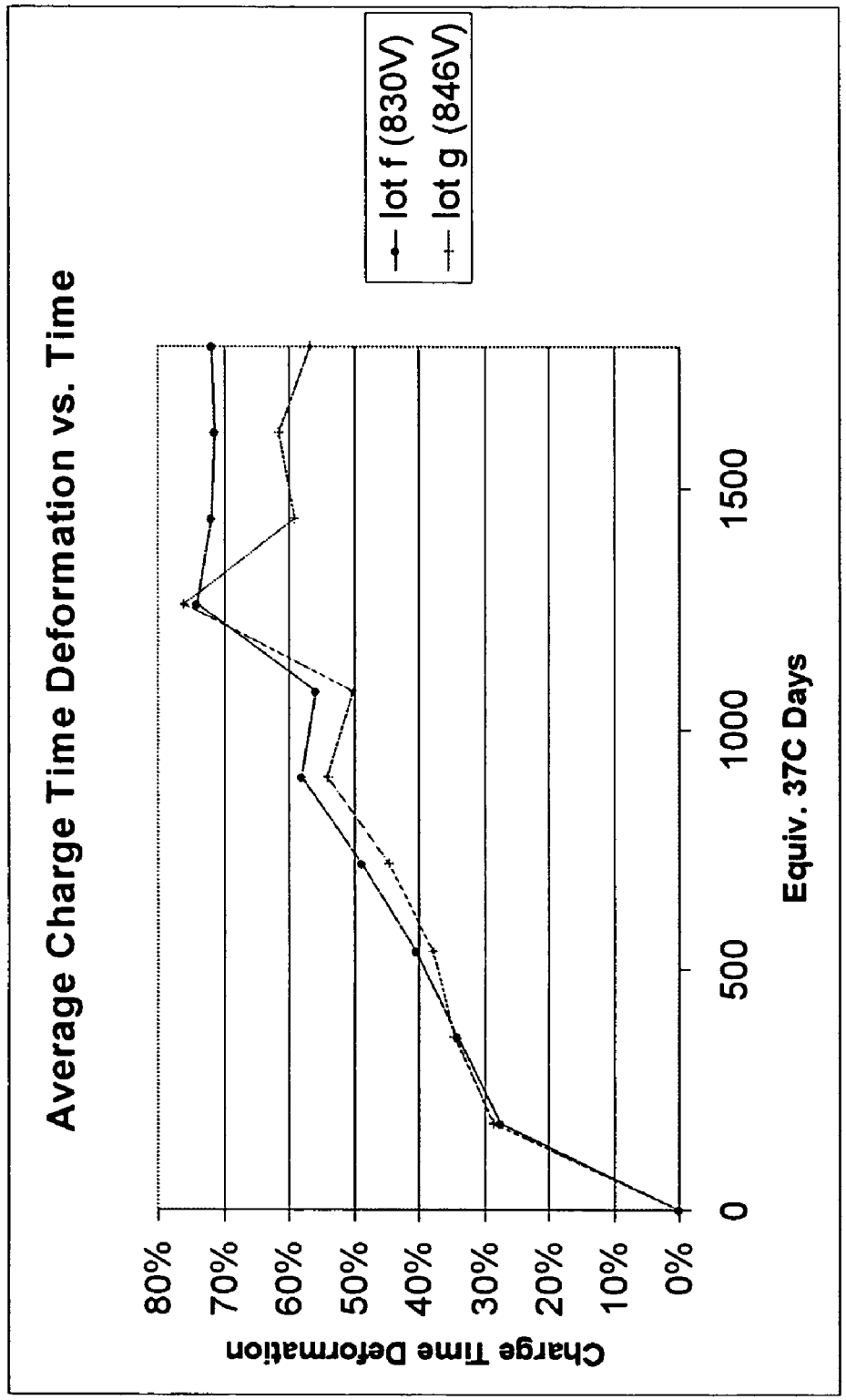
FIG. 2 shows the effects of higher reform voltages according to the present invention on charge time deformation for capacitors reformed at 6-month reform intervals.

As can be seen from FIG. 2, the graphical plots of average charge time deformation vs. equivalent 37° C. days for Test lots F (reformed to 830V) and G (reformed to 846V) show a significant improvement when reforming the capacitors to a Surge voltage of 846V vs. a Nominal voltage of 830V.

Figure 3:
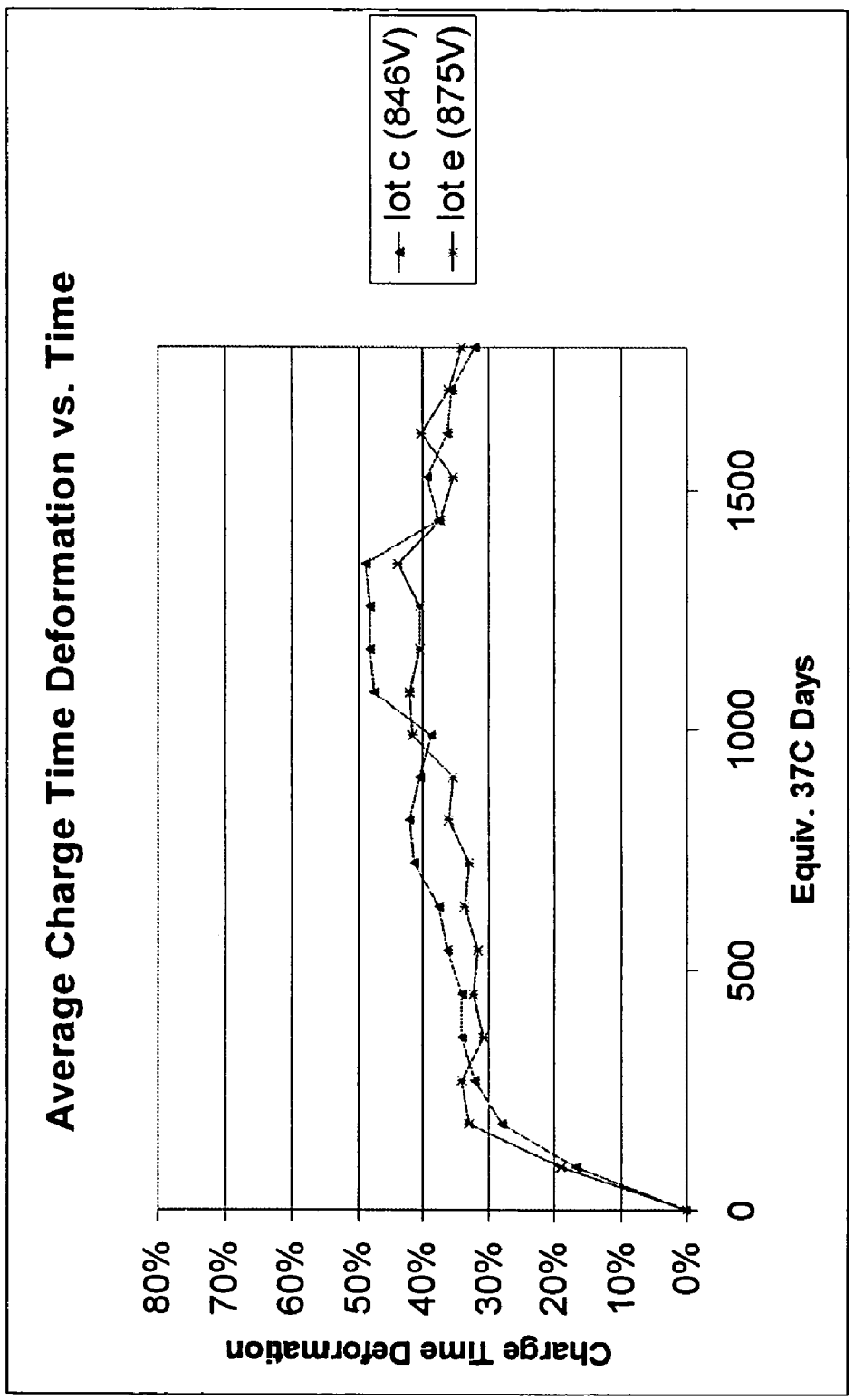
FIG. 3 shows the effects of higher reform voltages according to the present invention on charge time deformation for capacitors reformed at 3-month intervals.

As can be seen from FIG. 3, the graphical plots of average charge time deformation vs. equivalent 37° C. days for Test lots C (reformed to 846V) and E (reformed to 875V) show an improvement when reforming the capacitors to 875V vs. 846V.

Figure 4:
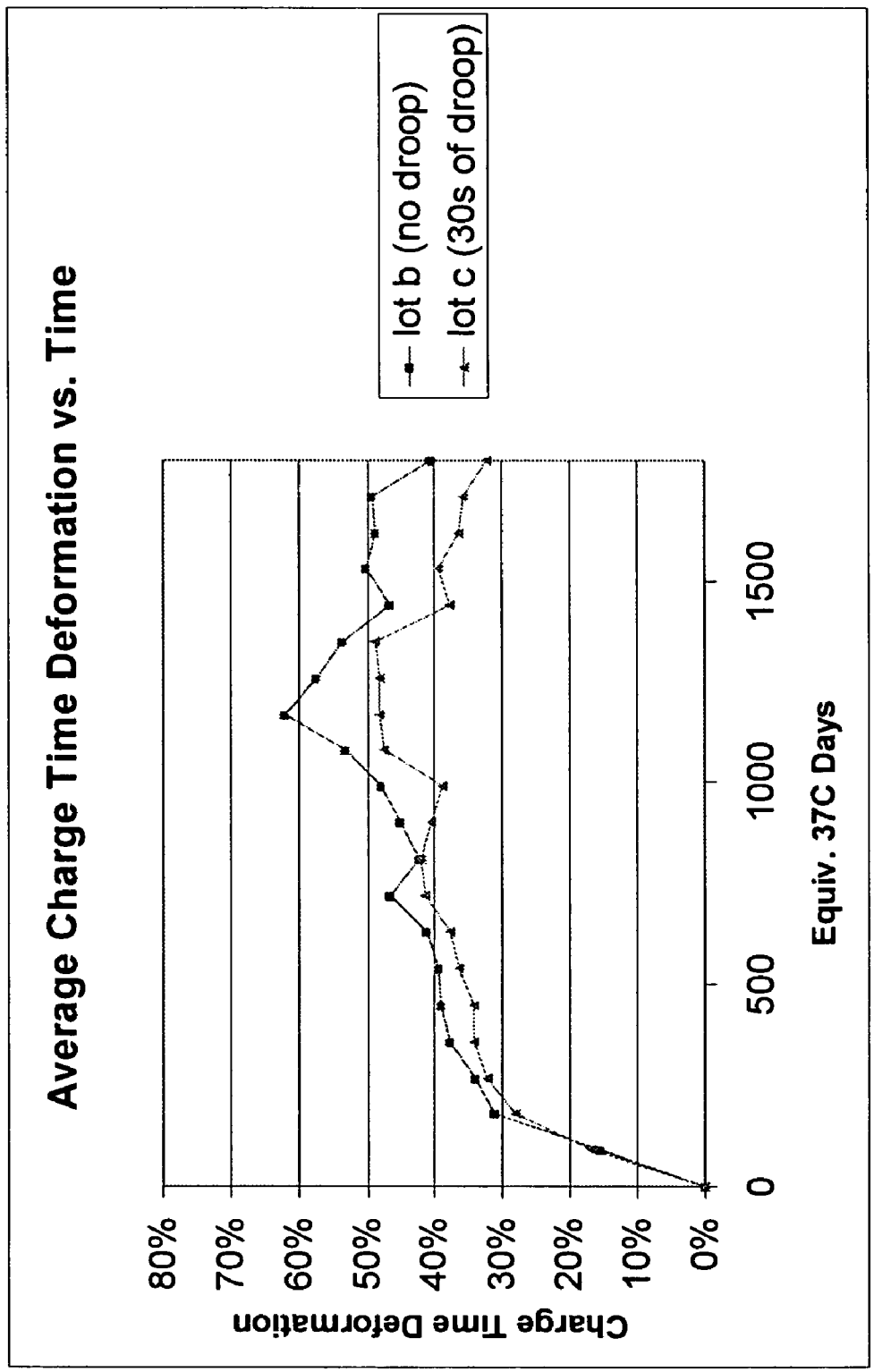
FIG. 4 shows the effects of increased droop time on charge time deformation for capacitors reformed at 3-month intervals according to the present invention.

As can be seen from FIG. 4, the graphical plots of average charge time deformation vs. equivalent 37° C. days for Test lots B (no droop) and C (30 seconds droop) show a significant improvement when the capacitors are allowed to droop for 30 seconds vs. immediately dumping the charge.

Figure 5:
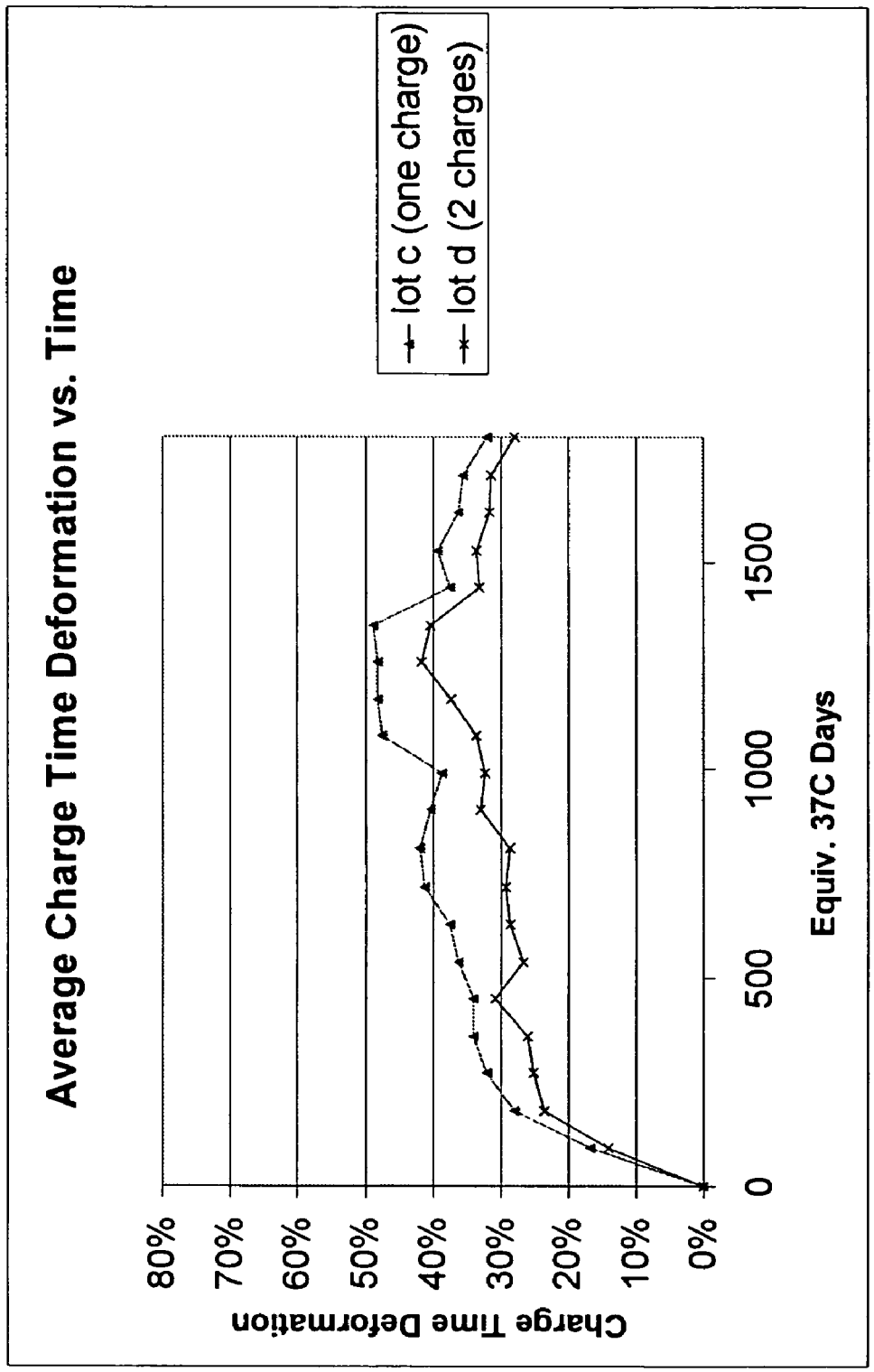
FIG. 5 shows the effects of a second charging of the capacitors in the reformation process on charge time deformation for capacitors reformed at 3-month intervals according to the present invention.

As can be seen from FIG. 5, the graphical plots of average charge time deformation vs. equivalent 37° C. days for Test lots C (one charge) and D (two charges) show a significant improvement when the capacitors are given an additional charge.

Figure 6:
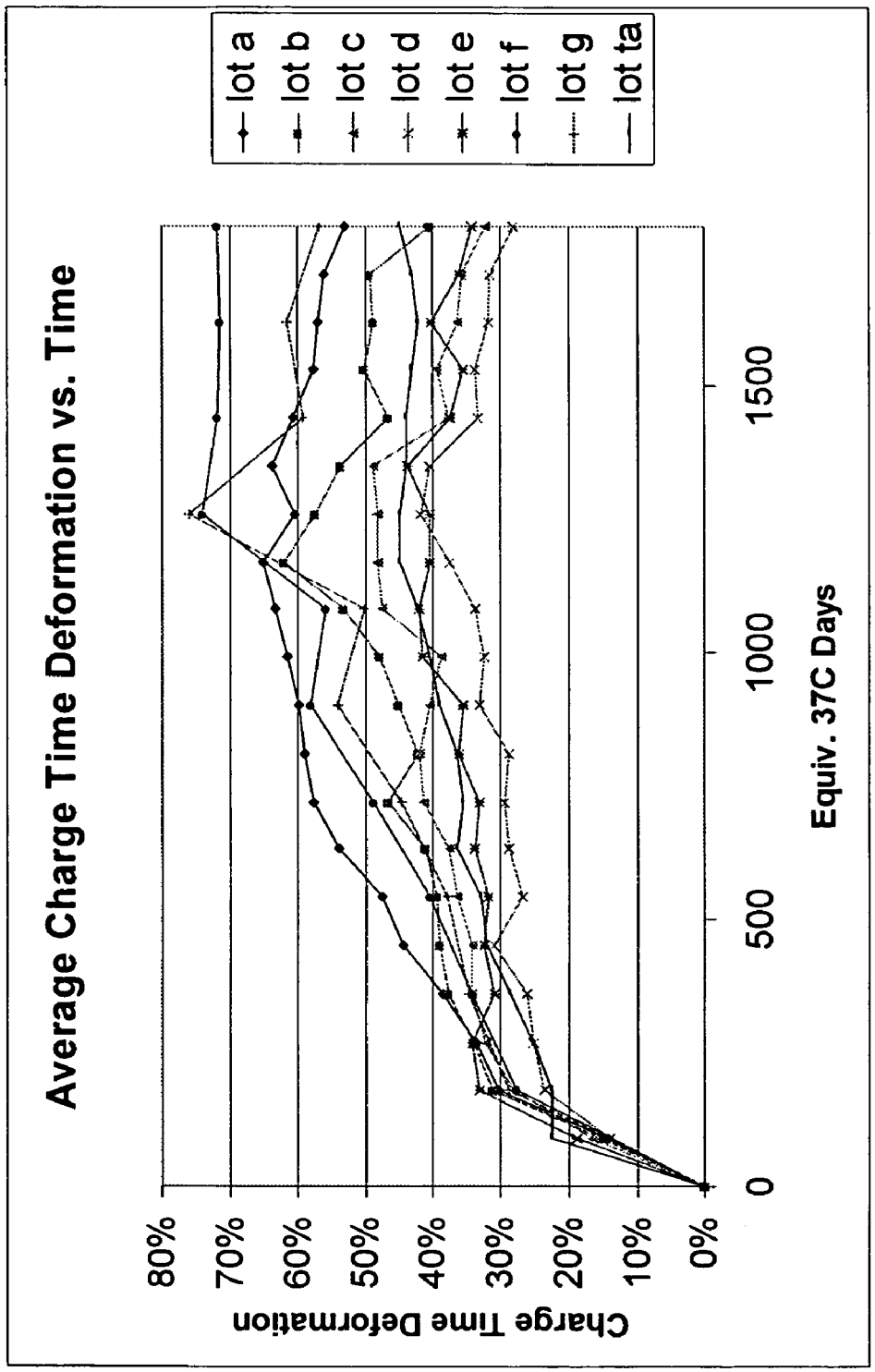
FIG. 6 shows the charge time deformation over time of various capacitors reformed according to the present invention.

The graphical plots of average charge time deformation vs. equivalent 37° C. days for all Test lots are shown in FIG. 6. A Tantalum capacitor ("lot ta") was included in this test as a comparison point.

Example 2

Thirty (30) aluminum electrolytic capacitor pairs were tested as in Example 1. The capacitor pairs were randomly divided into 10 test lots as follows:

Lot A—Control lot that, for each 3-month 37° C. equivalent down, was breadboard charged at ERI battery condition to a nominal voltage of 830V, allowed to bleed down for 3600 seconds, and then dumped.

Lot B—Test lot that, for each 3-month 37° C. equivalent down, was breadboard charged at ERI battery condition to 830V, allowed to bleed down for 4 seconds, charged to 830V again, allowed to bleed down for 300 seconds and then dumped.

Lot C—Test lot that, for each 3-month 37° C. equivalent down, was breadboard charged at ERI battery condition to 860V, allowed to bleed down for 10 seconds, charged to 860V again, allowed to bleed down for 300 seconds and then dumped.

Lot D—Test lot that, for each 3-month 37° C. equivalent down, was breadboard charged at ERI battery condition to 880V, allowed to bleed down for 30 seconds, charged to 880V again, allowed to bleed down for 300 seconds and then dumped.

Lot E—Test lot that, for each 3-month 37° C. equivalent down, was breadboard charged at ERI battery condition to 830V, allowed to bleed down for 10 seconds, charged to 830V again, allowed to bleed down for 300 seconds and then dumped.

Lot F—Test lot that, for each 3-month 37° C. equivalent down, was breadboard charged at ERI battery condition to 860V, allowed to bleed down for 10 seconds, charged to 860V again, allowed to bleed down for 300 seconds and then dumped.

Lot G—Test lot that, for each 3-month 37° C. equivalent down, was breadboard charged at ERI battery condition to 830V, allowed to bleed down for 30 seconds, charged to 830V again, allowed to bleed down for 300 seconds and then dumped.

Lot H—Test lot that, for each 3-month 37° C. equivalent down, was breadboard charged at ERI battery condition to 860V, allowed to bleed down for 30 seconds, charged to 860V again, allowed to bleed down for 300 seconds and then dumped.

Lot I—Test lot that, for each 3-month 37° C. equivalent down, was breadboard charged at ERI battery condition to 880V, allowed to bleed down for 30 seconds, charged to 880V again, allowed to bleed down for 300 seconds and then dumped.

Table 4 shows an average of the charge times obtained for each test lot when capacitors were charged at BOL battery condition and an average of the charge times obtained for each test lot when capacitors were charged at ERI battery condition. Table 5 shows the average charge times for the control lot A. Table 6 shows the average decrease in charge times over lot A charge times for each of the test lots. Table 7 shows the average charge time deformation percentages for each lot.

TABLE 4

BOL and ERI baselines

| Lot No. | BOL baseline charge time (s) | ERI baseline charge time (s) |
|---|---|---|
| A | 7.35 | 11.66 |
| B | 7.37 | 11.74 |
| C | 7.40 | 11.81 |
| D | 7.41 | 11.80 |
| E | 7.37 | 11.70 |
| F | 7.35 | 11.64 |
| G | 7.34 | 11.64 |
| H | 7.37 | 11.65 |
| I | 7.36 | 11.69 |

TABLE 5

Charge Times (seconds) of Lot A

| DOWN | LOT A |
|---|---|
| 1 | 15.07 |
| 2 | 15.07 |
| 3 | 15.47 |
| 4 | 15.87 |
| 5 | 16.34 |
| 6 | 15.73 |
| 7 | 15.33 |
| 8 | 15.87 |
| 9 | 15.33 |
| 10 | 15.73 |
| 11 | 15.73 |
| 12 | 14.93 |
| 13 | 15.46 |
| 14 | 15.60 |
| 15 | 15.07 |
| 16 | 14.67 |
| 17 | 14.13 |
| 18 | 14.13 |
| 19 | 15.07 |
| 20 | 14.27 |

TABLE 6

Charge Time Decrease over Lot A Charge Times (seconds)

| DOWN | LOT B | LOT C | LOT D | LOT E | LOT F | LOT G | LOT H | LOT I |
|---|---|---|---|---|---|---|---|---|
| 1 | 0.14 | 0.14 | 0.16 | 1.07 | 0.80 | 0.80 | 0.93 | 0.40 |
| 2 | 0.27 | 0.27 | 0.53 | 0.67 | 0.67 | 0.93 | 0.80 | −0.53 |
| 3 | 0.60 | 0.40 | 0.93 | 0.67 | 0.67 | 0.53 | 0.80 | 0.67 |
| 4 | 0.54 | 0.67 | 1.20 | 0.80 | 1.20 | 1.47 | 1.60 | 1.33 |
| 5 | 1.54 | 1.54 | 2.21 | 1.67 | 1.54 | 1.54 | 1.67 | 1.81 |
| 6 | 0.67 | 0.40 | 1.33 | 0.53 | 1.60 | 1.07 | 1.33 | 1.33 |
| 7 | −0.40 | 0.27 | 1.40 | 0.54 | 0.67 | 0.27 | 0.80 | 0.80 |
| 8 | 0.54 | 0.80 | 1.86 | 0.93 | 1.20 | 1.20 | 1.33 | 1.47 |
| 9 | 0.54 | 0.93 | 1.13 | 0.40 | 1.20 | 0.27 | 0.80 | 0.67 |
| 10 | 0.93 | 1.47 | 1.46 | 0.94 | 1.33 | 1.07 | 1.33 | 1.20 |
| 11 | 0.80 | 1.20 | 1.33 | 1.20 | 1.60 | 1.20 | 1.20 | 1.53 |
| 12 | 0.27 | 0.67 | 0.67 | 0.27 | 0.80 | 0.27 | 0.67 | 1.07 |
| 13 | 0.66 | 0.93 | 1.46 | 0.80 | 0.93 | 0.80 | 1.06 | 1.33 |
| 14 | 1.20 | 1.33 | 1.47 | 1.47 | 1.33 | 1.47 | 1.47 | 1.47 |
| 15 | 0.40 | 0.53 | 0.94 | 0.40 | 1.33 | 1.07 | 0.93 | 1.20 |
| 16 | 0.14 | 0.28 | 1.07 | 0.40 | 0.80 | 0.94 | 0.80 | 0.94 |
| 17 | −0.13 | −0.05 | 0.26 | −0.14 | 0.40 | 0.00 | 0.40 | 0.13 |
| 18 | −0.53 | −0.45 | 0.26 | 0.40 | 0.66 | 0.93 | 0.13 | 0.40 |
| 19 | 1.34 | 0.88 | 1.74 | 0.67 | 1.74 | 1.07 | 1.47 | 1.47 |
| 20 | 0.00 | 0.28 | 0.80 | 0.13 | 1.07 | 0.67 | 0.53 | 0.80 |
| Average | 0.48 | 0.62 | 1.11 | 0.69 | 1.08 | 0.88 | 1.00 | 0.97 |

TABLE 7

Charge Time Deformation

| DOWN | LOT A | LOT B | LOT C | LOT D | LOT E | LOT F | LOT G | LOT H | LOT I |
|---|---|---|---|---|---|---|---|---|---|
| 1 | 29.19% | 27.14% | 26.40% | 26.36% | 19.66% | 22.60% | 22.57% | 21.35% | 25.43% |
| 2 | 29.17% | 26.01% | 25.27% | 23.16% | 23.07% | 23.75% | 21.42% | 22.51% | 33.41% |
| 3 | 32.61% | 26.57% | 27.53% | 23.18% | 26.49% | 27.19% | 28.30% | 25.94% | 26.56% |
| 4 | 36.04% | 30.56% | 28.65% | 24.30% | 28.76% | 26.04% | 23.71% | 22.50% | 24.30% |
| 5 | 40.08% | 26.00% | 25.27% | 19.75% | 25.34% | 27.19% | 27.14% | 25.94% | 24.29% |
| 6 | 34.89% | 28.27% | 29.79% | 22.04% | 29.90% | 21.46% | 26.00% | 23.65% | 23.15% |
| 7 | 31.48% | 33.96% | 27.54% | 18.08% | 26.49% | 26.05% | 29.43% | 24.80% | 24.27% |
| 8 | 36.03% | 30.55% | 27.53% | 18.67% | 27.63% | 26.05% | 25.99% | 24.80% | 23.14% |
| 9 | 31.47% | 26.01% | 21.89% | 20.35% | 27.61% | 21.46% | 29.43% | 24.80% | 25.42% |
| 10 | 34.89% | 26.04% | 20.76% | 20.93% | 26.48% | 23.75% | 26.00% | 23.65% | 24.27% |
| 11 | 34.89% | 27.14% | 23.02% | 22.04% | 24.22% | 21.46% | 24.86% | 24.80% | 21.44% |
| 12 | 28.04% | 24.88% | 20.76% | 20.89% | 25.33% | 21.46% | 26.00% | 22.51% | 18.59% |
| 13 | 32.59% | 26.02% | 23.02% | 18.65% | 25.34% | 24.90% | 25.99% | 23.64% | 20.86% |

TABLE 7-continued

Charge Time Deformation

| DOWN | LOT A | LOT B | LOT C | LOT D | LOT E | LOT F | LOT G | LOT H | LOT I |
|---|---|---|---|---|---|---|---|---|---|
| 14 | 33.75% | 22.62% | 20.77% | 19.77% | 20.79% | 22.61% | 21.42% | 21.36% | 20.87% |
| 15 | 29.17% | 24.88% | 23.02% | 19.75% | 25.34% | 18.02% | 20.28% | 21.36% | 18.59% |
| 16 | 25.76% | 23.75% | 21.78% | 15.26% | 21.92% | 19.17% | 17.98% | 19.06% | 17.44% |
| 17 | 21.16% | 21.47% | 20.08% | 17.52% | 21.94% | 18.02% | 21.42% | 17.91% | 19.72% |
| 18 | 21.17% | 24.89% | 23.48% | 17.52% | 17.37% | 15.73% | 13.40% | 20.20% | 17.44% |
| 19 | 29.21% | 16.92% | 20.08% | 13.01% | 23.07% | 14.59% | 20.27% | 16.77% | 16.30% |
| 20 | 22.31% | 21.48% | 18.39% | 14.13% | 20.81% | 13.44% | 16.83% | 17.91% | 15.16% |

Figure 7:
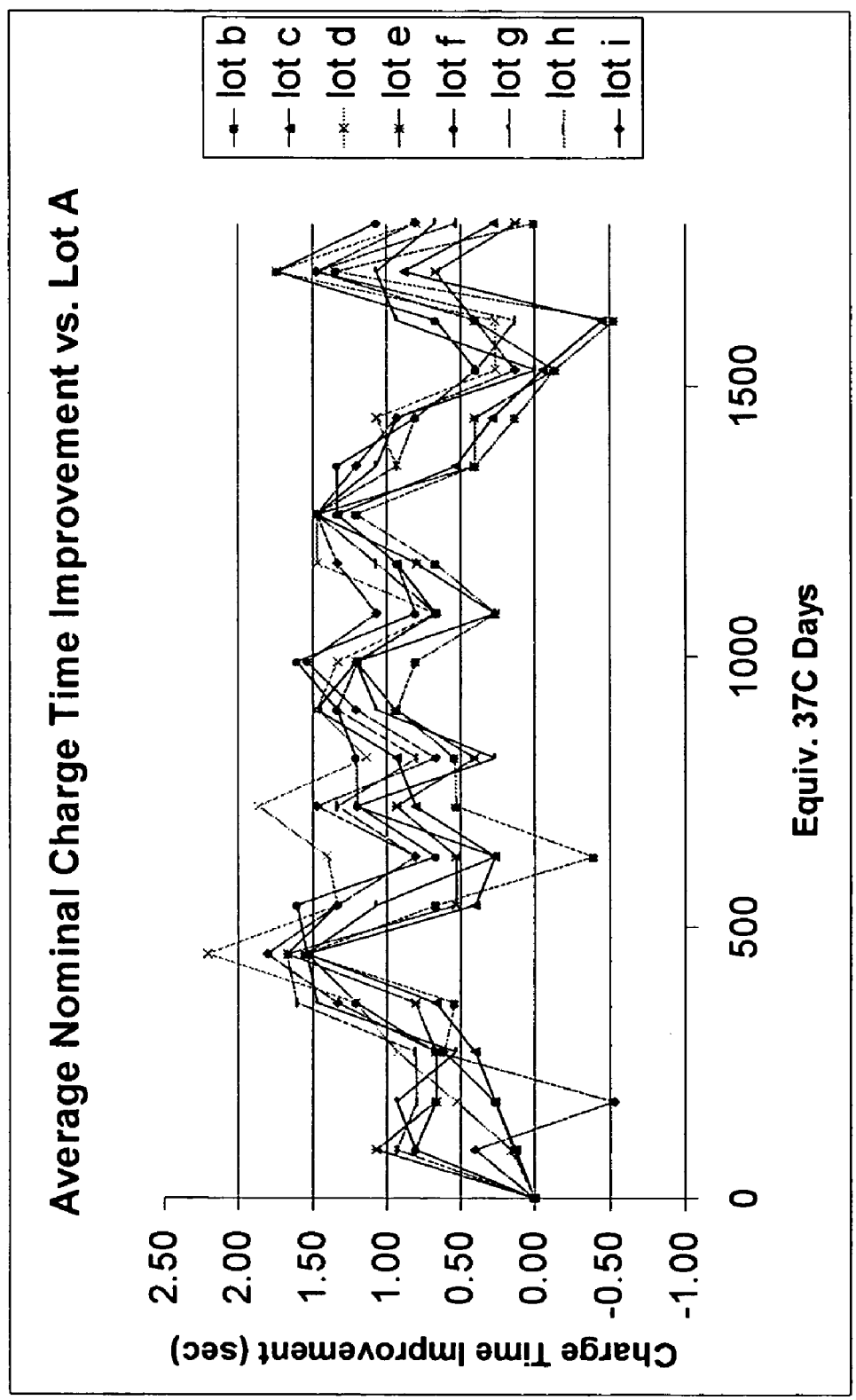
FIG. 7 shows the average nominal charge time improvement of the test lots over the charge time of lot A.
Figure 8:
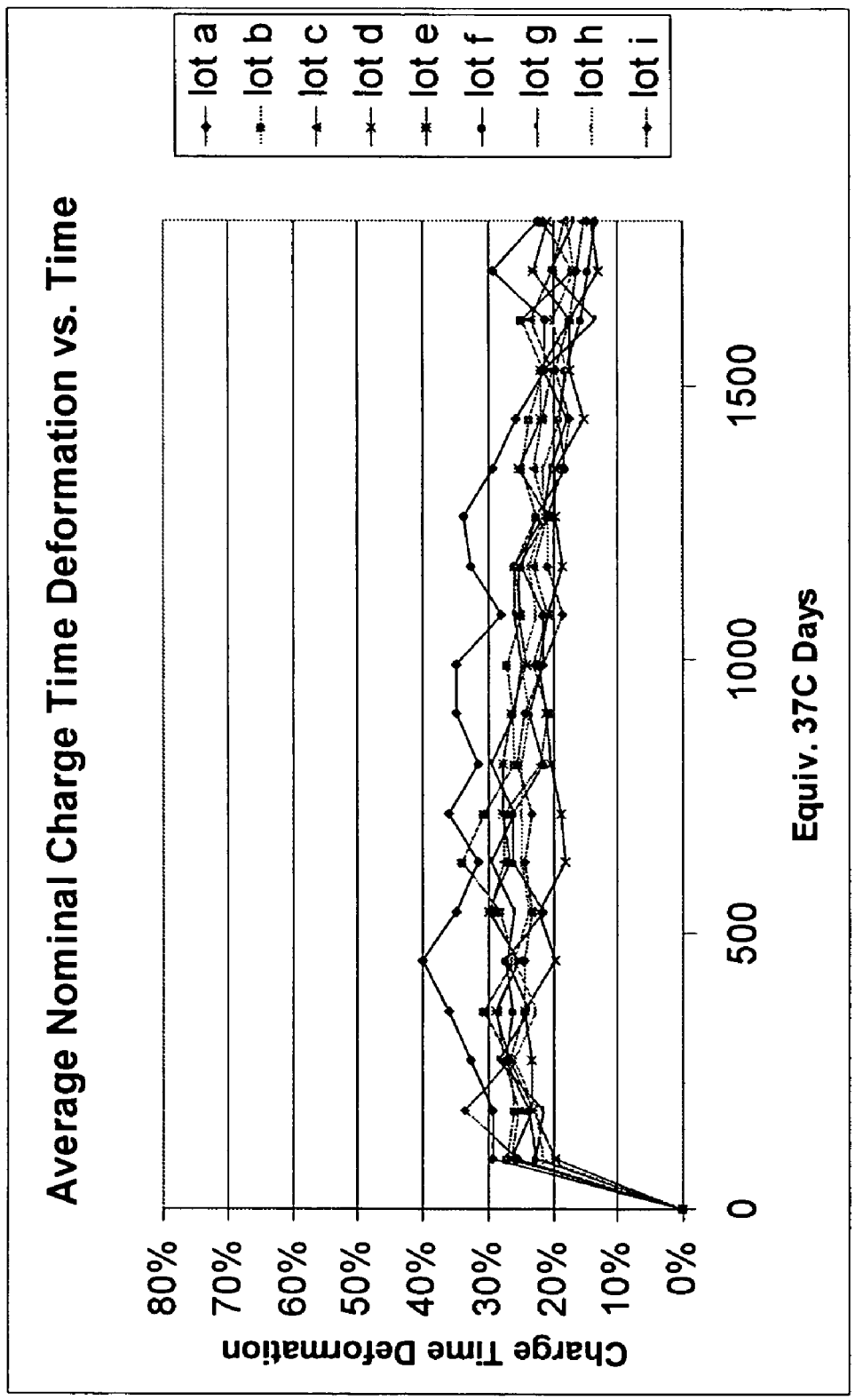
FIG. 8 shows the average nominal charge time deformation of capacitors reformed according to the present invention.

FIG. 7 is a graph of the average nominal charge time improvements of the test lot capacitors over lot A capacitor charge times. FIG. 8 shows the average charge time deformation over time when the capacitors of each test lot are charged to a nominal voltage.

In this experiment, lot A capacitors (the control) were allowed to droop for 3600 seconds after a charge to 830V, before the charge was dumped. The test lots, however, were allowed to droop for 4-30 seconds at the end of the second charge before the charge was dumped. This difference in droop time may have effected the charge time improvement measurements. The actual charge time improvements may be greater than the recorded results since allowing the test lot capacitors to droop for 3600 seconds (as in the control lot) is expected to further decrease the charge times of the test lot capacitors.

Figure 9:
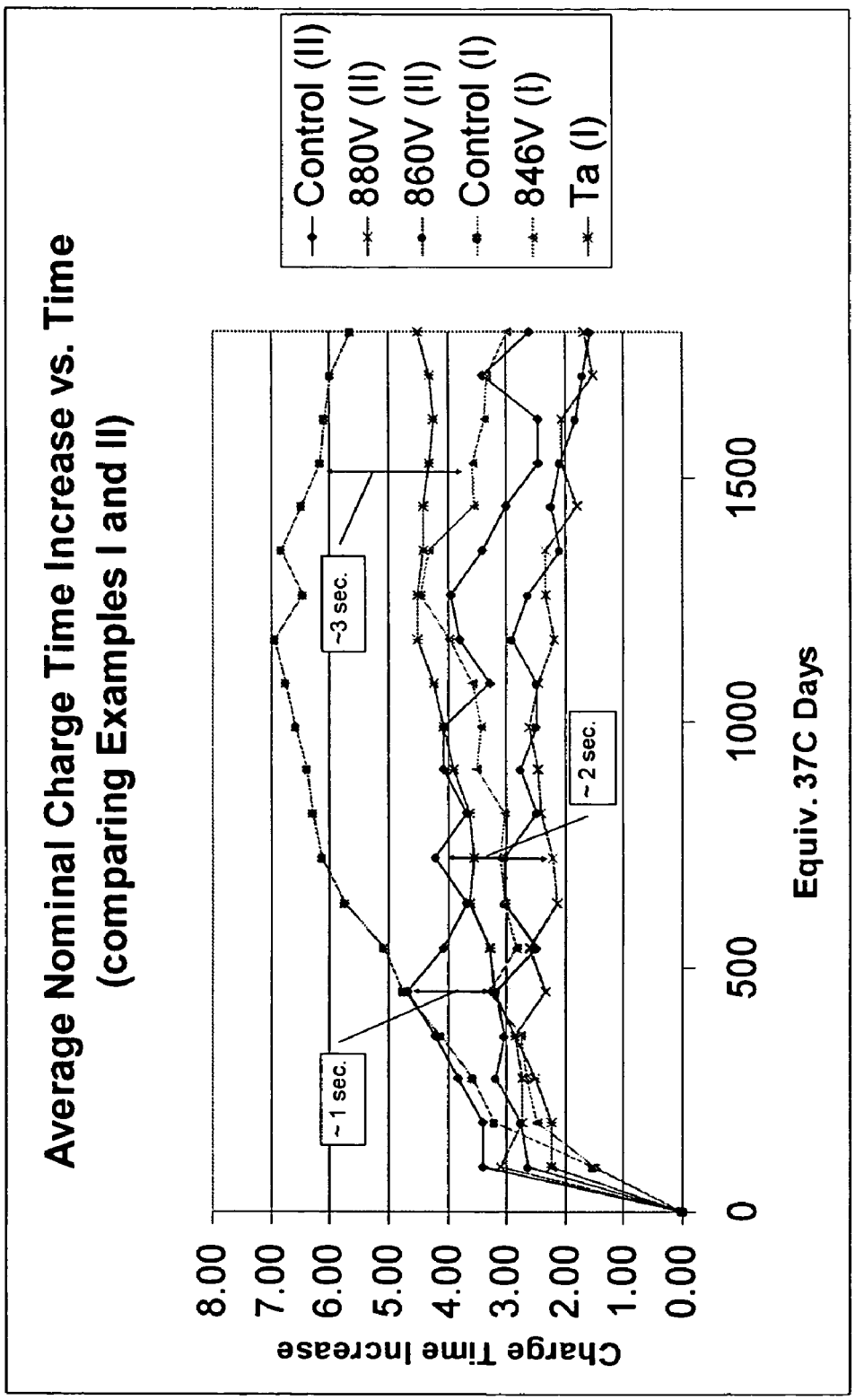
FIG. 9 shows the average nominal charge time increases over time of various capacitors reformed according to the present invention.

FIG. 9 shows the average charge time increases over time for charging the capacitors from Example 1 and Example 2 to a nominal voltage. Capacitors charged to a nominal voltage of 830V (Control I), capacitors charged to a surge voltage of 846V (846V (I)) and the tantalum capacitor control (Ta(I)) from Example 1 were compared with capacitors charged to a nominal voltage of 830V (Control II), capacitors charged to a surge voltage of 880V (880V (II)), and capacitors charge to a surge voltage of 860V (860V (II)) from Example 2.

Example 3

The effects of the delivery of a shock voltage that is higher than a nominal voltage on capacitors that have not been reformed by charging to a voltage above the nominal voltage was assessed. If a nominal shock (charging the capacitor to a nominal operating voltage) does not deliver adequate therapy to the patient, it is possible to immediately administer a shock of higher delivered energy by charging the capacitor to surge voltages.

Twelve aluminum electrolytic capacitors were paired and split into Lot A and Lot B. Lot A was reformed at a nominal voltage while Lot B was reformed at a voltage that is above the nominal voltage. All capacitors were baseline tested using the MCT Forming and Discharge test as outlined previously. Using the breadboard, all capacitors were charged three times (to put the capacitor oxide in a formed state) and the breadboard charge times were recorded (this charge was the baseline and was used to calculate the percent deformation for each accelerated life down).

For each down, the capacitors were placed in a 90° C. oven for 16 hours (the accelerated equivalent of 37° C. for 90 days). After the time expired, the capacitor pairs were removed from the oven and placed in a body box until the capacitors were at 37° C.

As the charge time deformation increases: Lot A capacitors were reformed by charging to a nominal voltage of 830V and then dumping the charge; Lot B capacitors were reformed by charging to a surge voltage of 880V, allowing to droop 30 seconds, charging to a surge voltage of 880V for a second time, allowing to droop for 30 seconds, and then dumping the charge. The charge time required to charge Lot A and Lot B capacitors to a nominal voltage of 830V was measured.

After the charge time deformation leveled off. Lot A and Lot B capacitors were reformed by charging to a nominal voltage of 830V and dumping the charge. The charge time required to charge Lot A and Lot B capacitors to a nominal voltage of 830V was recorded. Lot A and Lot B capacitors were then charged to a surge voltage of 880V and the charge was then dumped. The charge time required to charge the capacitors to a surge voltage of 880V was measured. Table 8 shows the average charge times to a surge voltage of 880V for Lot A and Lot B. In earlier downs not shown in Table 8, the capacitors were charged up to a nominal voltage of 830V. Table 9 shows the average charge time deformation for both Lot A and Lot B capacitors. Table 10 shows the average charge time to a nominal voltage of 830V for Lot A and Lot B capacitors. Table 11 shows the average improvements in charge time for charging Lot B capacitors to a nominal voltage over charging Lot A capacitors to a nominal voltage.

TABLE 8

Charge Times to a Surge Voltage of 880 V

| Lot A | | Lot B | |
|---|---|---|---|
| 37° C. days | Charge Time (s) | 37° C. days | Charge Time (s) |
| 850 | 12.16 | 850 | 11.76 |
| 940 | 11.63 | 940 | 11.49 |
| 1030 | 11.76 | 1030 | 11.96 |
| 1120 | 11.96 | 1120 | 11.76 |
| 1210 | 12.43 | 1210 | 12.09 |
| 1300 | 11.09 | 1300 | 10.72 |
| 1390 | 12.48 | 1390 | 12.11 |
| 1740 | 10.78 | 1740 | 10.75 |
| 1830 | 11.22 | 1830 | 11.15 |

TABLE 9

Charge Times Deformation

| Lot A | | Lot B | |
|---|---|---|---|
| 37° C. days | deformation | 37° C. days | deformation |
| 90 | 18.95% | 90 | 16.14% |
| 180 | 22.03% | 180 | 18.47% |
| 270 | 28.74% | 270 | 23.82% |
| 360 | 28.81% | 360 | 24.52% |
| 450 | 35.34% | 450 | 25.14% |
| 540 | 38.54% | 540 | 29.11% |

TABLE 9-continued

Charge Times Deformation

| Lot A | | Lot B | |
|---|---|---|---|
| 37° C. days | deformation | 37° C. days | deformation |
| 630 | 38.21% | 630 | 27.45% |
| 850 | 44.34% | 850 | 33.68% |
| 940 | 28.53% | 940 | 27.01% |
| 1030 | 29.38% | 1030 | 30.67% |
| 1120 | 24.86% | 1120 | 25.52% |
| 1210 | 32.37% | 1210 | 31.45% |
| 1300 | 21.79% | 1300 | 20.16% |
| 1390 | 33.50% | 1390 | 35.70% |
| 1740 | 22.78% | 1740 | 27.01% |
| 1830 | 18.26% | 1830 | 19.81% |

TABLE 10

Charge Times to a Nominal Voltage of 830 V

| Lot A | | Lot B | |
|---|---|---|---|
| 37° C. days | Charge Time (s) | 37° C. days | Charge Time (s) |
| 90 | 10.71 | 90 | 10.57 |
| 180 | 10.97 | 180 | 10.77 |
| 270 | 11.57 | 270 | 11.27 |
| 360 | 11.57 | 360 | 11.33 |
| 450 | 12.16 | 450 | 11.39 |
| 540 | 12.44 | 540 | 11.75 |
| 630 | 12.43 | 630 | 11.59 |
| 850 | 12.96 | 850 | 12.03 |
| 940 | 11.56 | 940 | 11.43 |
| 1030 | 11.63 | 1030 | 11.76 |
| 1120 | 11.23 | 1120 | 11.40 |
| 1210 | 11.89 | 1210 | 11.83 |
| 1300 | 10.96 | 1300 | 10.81 |
| 1390 | 12.01 | 1390 | 12.21 |
| 1740 | 11.05 | 1740 | 11.41 |
| 1830 | 10.70 | 1830 | 10.78 |

TABLE 11

Charge Time Improvements to Nominal (830 V)

| 37° C. days | Improvement in charge time to nominal of lot B over lot A (s) |
|---|---|
| 90 | 0.13 |
| 180 | 0.20 |
| 270 | 0.31 |
| 360 | 0.24 |
| 450 | 0.77 |
| 540 | 0.69 |
| 630 | 0.84 |
| 850 | 0.93 |
| 940 | 0.13 |
| 1030 | −0.13 |
| 1120 | −0.17 |
| 1210 | 0.07 |
| 1300 | 0.15 |
| 1390 | −0.20 |
| 1740 | −0.37 |
| 1830 | −0.08 |

Figure 10:
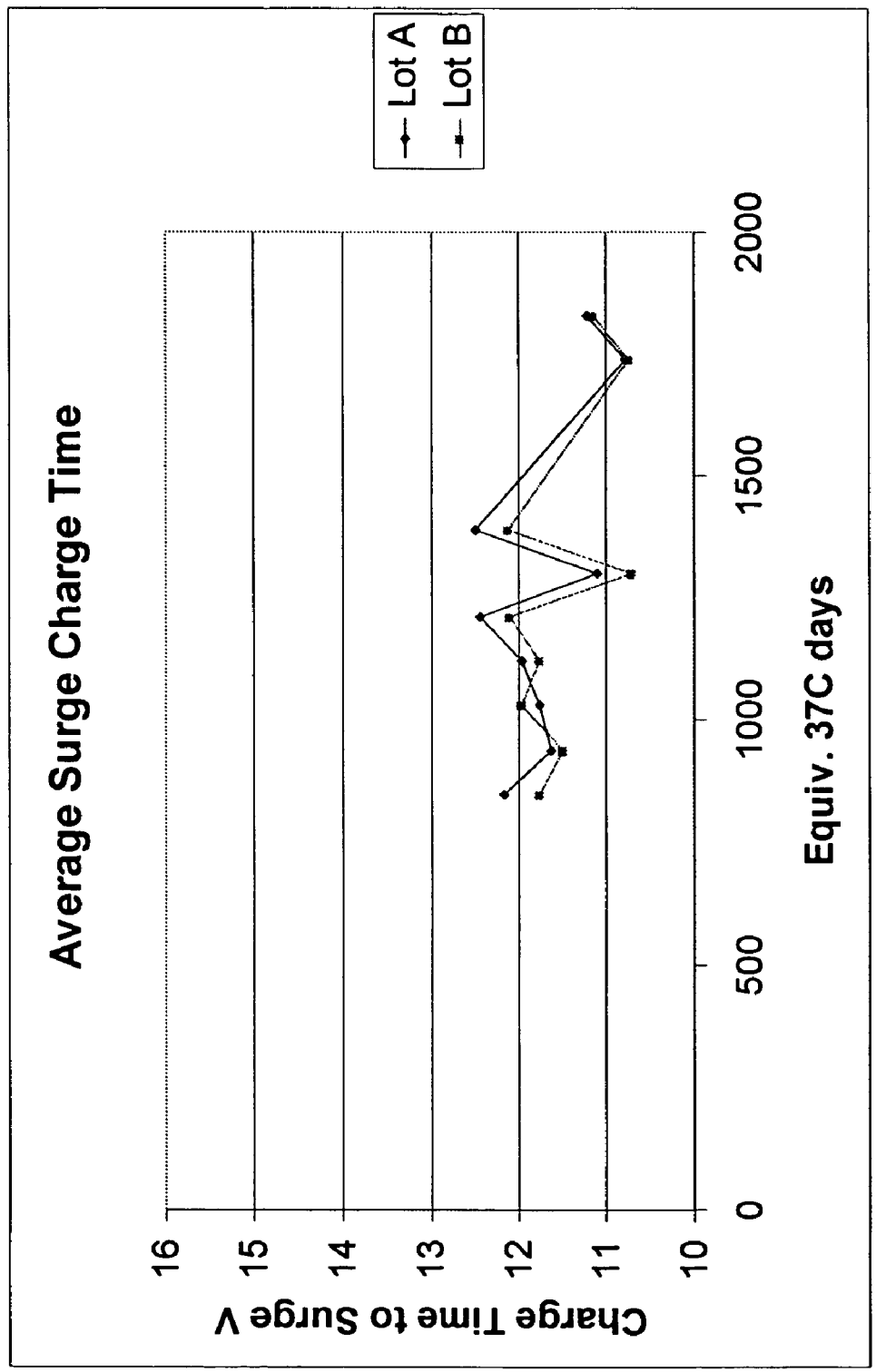
FIG. 10 shows the average charge time to surge voltage of capacitors reformed according to the present invention.

FIGS. 10-13 are graphs of the measurements obtained. As can be seen in FIG. 10, there was an average charge time increase for Test Lot A (reformed at a nominal voltage) as compared to Test Lot B (reformed at a surge voltage) of about 0.4 seconds when charging to a surge voltage of 880V at periods when the capacitors were in their worst charge time deformation state.

Figure 11:
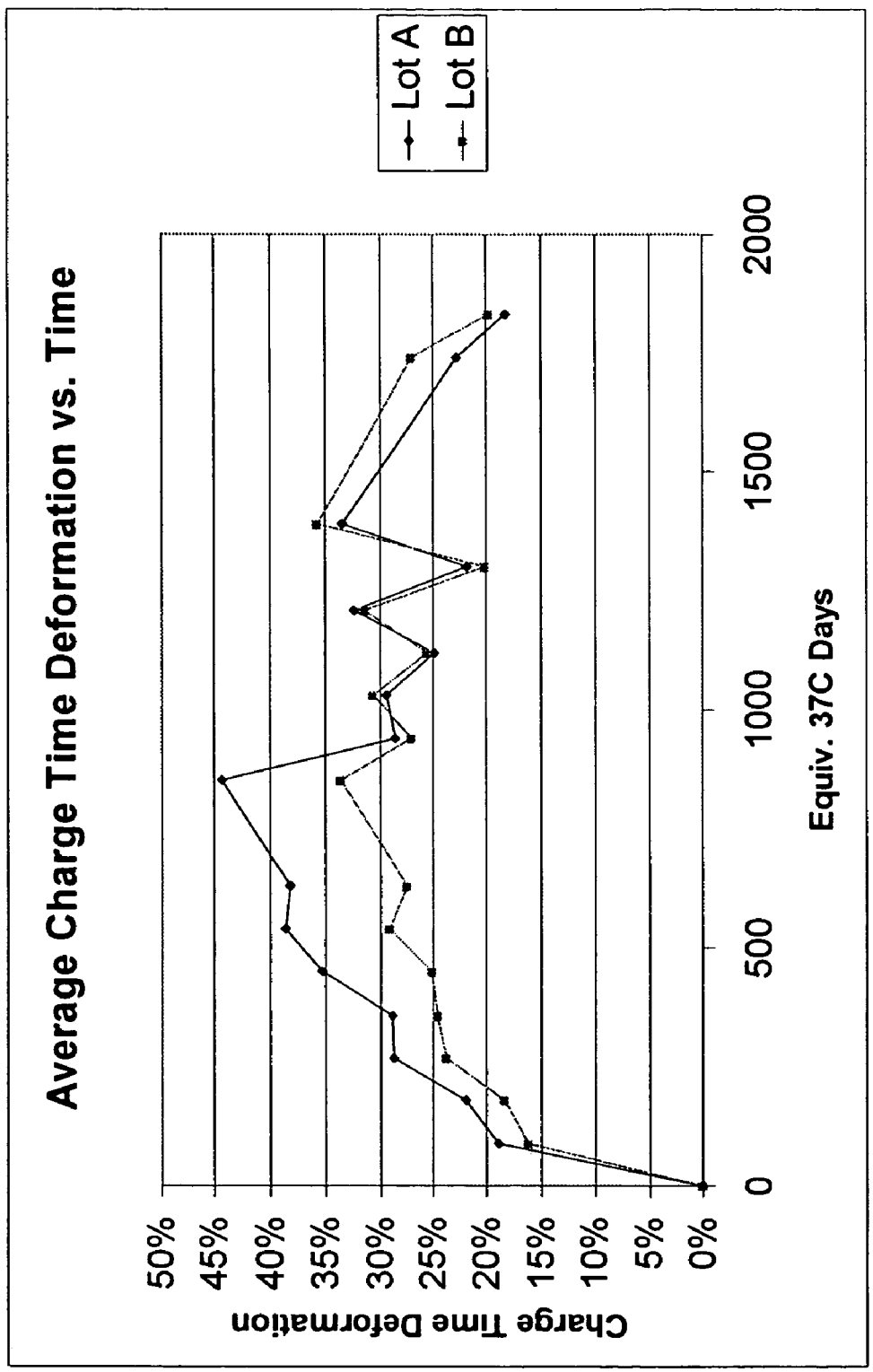
FIG. 11 shows the average charge time deformation of capacitors reformed according to the present invention.
Figure 12:
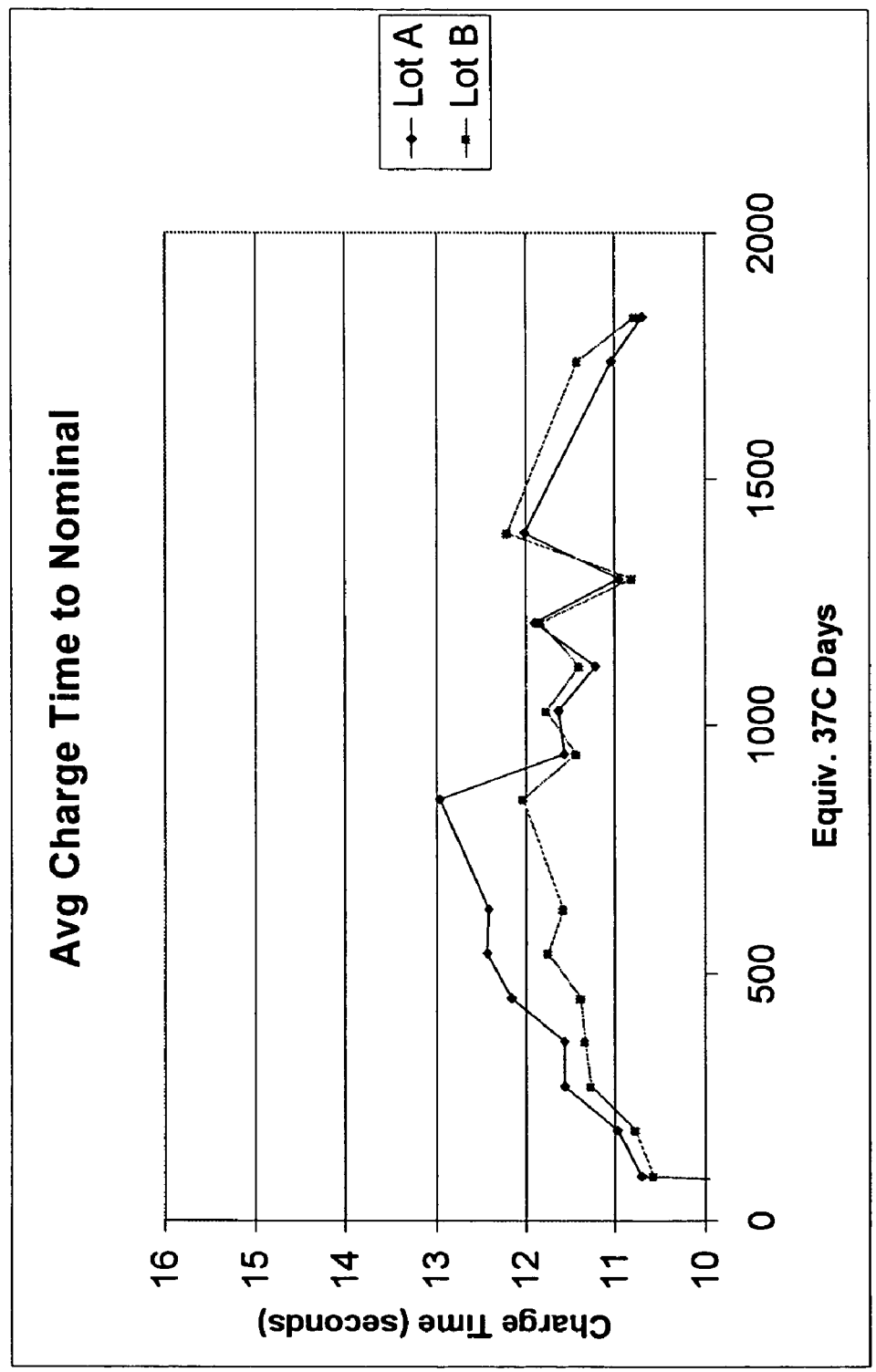
FIG. 12 shows the average charge time to nominal voltage of capacitors reformed according to the present invention.
Figure 13:
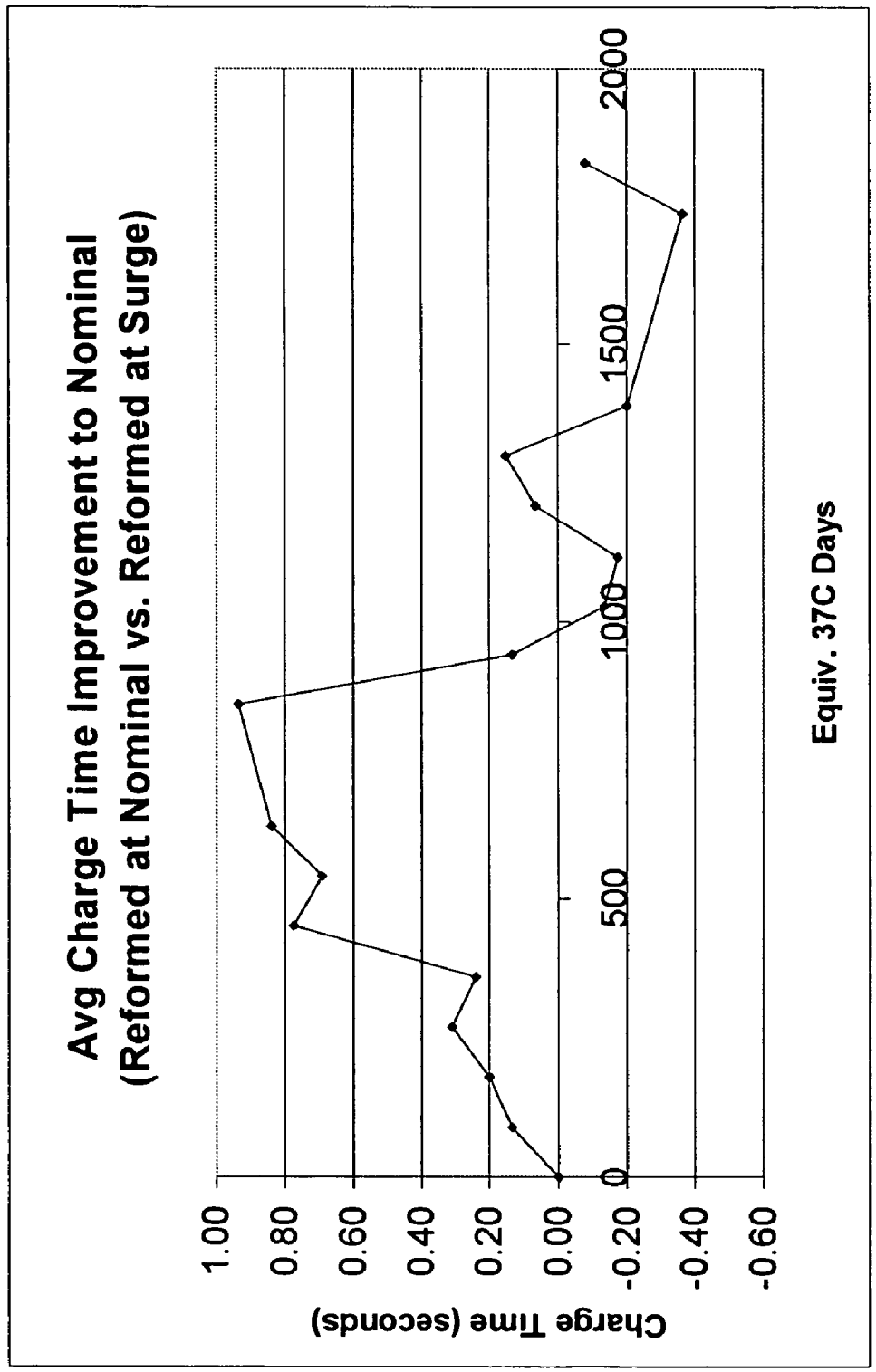
FIG. 13 shows the average charge time improvement for charging to nominal voltage in capacitors reformed according to the present invention.

As can be seen in FIGS. 11, 12 and 13, the average charge time deformation for Test Lot A (reformed at a nominal voltage) as compared to Test Lot B (reformed at a surge voltage) was 10.76 percentage points higher (equating to an increase in average charge times of about 0.9 seconds. It should be noted that this difference disappears once the Lot A group essentially becomes the Lot B group once the charge to surge voltage levels begins (after down #7).

The data from this experiment suggest that capacitors reformed at a surge voltage have reduced charge time deformation and decreased charge times when charging the capacitors to either nominal or surge voltages for shock delivery therapy compared to capacitors reformed according to the conventional method of charging to a nominal voltage.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents. Additionally, all patents, patent applications and publications mentioned above are incorporated herein by reference.

What is claimed is:

1. A method for reforming a capacitor of an implantable medical device wherein said capacitor has a nominal voltage, said method comprising the steps of:
   (a) charging said capacitor to a first voltage of about 2% to about 6% higher than said nominal voltage;
   (b) partially discharging said capacitor; and
   (c) charging said capacitor to a second voltage of about 2% to about 6% higher than said nominal voltage.

2. The method of claim 1, wherein said partially discharging step comprises discharging said capacitor through system leakage.

3. The method of claim 2, wherein said partially discharging step through system leakage is carried out for about 2 seconds to about 300 seconds.

4. The method of claim 3, wherein said partially discharging step through system leakage is carried out for about 4 seconds to about 30 seconds.

5. The method of claim 4, wherein said partially discharging step through system leakage is carried out for about 10 seconds.

6. The method of claim 1, wherein said partially discharging step comprises discharging said capacitor through a non-therapeutic load.

7. The method of claim 1, further comprising the step of discharging said capacitor after said step of charging said capacitor to a second voltage of about 2% to about 6% higher than said nominal voltage.

8. The method of claim 7, wherein said discharging step after said step of charging said capacitor to a second voltage of about 2% to about 6% higher than said nominal voltage comprises discharging said capacitor through system leakage.

9. The method of claim 8, wherein said discharging step through system leakage is carried out until the charge on said capacitor dissipates.

10. The method of claim 7, wherein said discharging step after said step of charging said capacitor to a second voltage above said nominal voltage comprises discharging said capacitor through a non-therapeutic load.

11. The method of claim 1, wherein said method is performed after the passing of a capacitor maintenance interval.

12. The method of claim 11, wherein said capacitor maintenance interval is 3 months.

13. The method of claim 11, wherein said capacitor maintenance interval is 4 months.

14. The method of claim 11, wherein said capacitor maintenance interval is 6 months.

15. The method of claim 1, further comprising charging a second capacitor to a first voltage of about 2% to about 6% higher than said nominal voltage of said second capacitor.

16. The method of claim 15, wherein said first capacitor and second capacitor are connected in series having a total nominal voltage of about 830 Volts and total first voltage of about 846 Volts to about 880 Volts.

17. The method of claim 16, wherein said total first voltage is about 860 Volts.

18. The method of claim 16, wherein said first total voltage is about 880 Volts.

19. An electrolytic capacitor reformed by the method of claim 1.

20. An implantable medical device comprising an electrolytic capacitor reformed by the method of claim 1.

21. A method for reforming a capacitor of an implantable cardioverter defibrillator wherein said capacitor has a nominal voltage for shock delivery, said method comprising:

charging said capacitor to a first surge voltage of about 2% to about 6% higher than said nominal voltage for shock delivery; and discharging said capacitor, wherein said discharging step comprises discharging said capacitor through system leakage or through a non-therapeutic load.

22. The method of claim 21, wherein said discharging step comprises discharging said capacitor through system leakage.

23. The method of claim 21, wherein said discharging step comprises discharging said capacitor through a non-therapeutic load.

24. A method for reforming a capacitor of an implantable medical device wherein said implantable medical device comprises two capacitors in series having a total nominal voltage of about 830 Volts, said method comprising the steps of:

(d) charging said capacitors to a first voltage of about 860 Volts;

(e) partially discharging said capacitors for about 10 seconds through system leakage;

(f) charging said capacitors to a second voltage of about 860 Volts; and (g) discharging said capacitors through system leakage until the charge on said capacitors dissipates.

25. An electrolytic capacitor reformed by the method of claim 24.

26. An implantable medical device comprising an electrolytic capacitor reformed by the method of claim 24.

27. A method for reforming a capacitor of an implantable medical device wherein said implantable medical device comprises two capacitors in series having a total nominal voltage of about 830 Volts, said method comprising the steps of:

(a) charging said capacitors to a first voltage of about 880 Volts;

(b) partially discharging said capacitors for about 10 seconds through system leakage;

(c) charging said capacitors to a second voltage of about 880 Volts; and (d) discharging said capacitors through system leakage until the charge on said capacitors dissipates.

28. An electrolytic capacitor reformed by the method of claim 27.

29. An implantable medical device comprising an electrolytic capacitor reformed by the method of claim 27.

* * * * *